US012773130B2

(12) United States Patent
Kang et al.

(10) Patent No.: US 12,773,130 B2
(45) Date of Patent: Oct. 27, 2026

(54) GAIT MEASUREMENT SYSTEM AND METHOD USING LIDAR ADJACENT TO FLOOR

(71) Applicant: Medicalsolutionsystem, Gimhae City (KR)

(72) Inventors: Minsoo Kang, Busan (KR); JoonMo Seo, Busan (KR)

(73) Assignee: Medicalsolutionsystem, Gimhae City (KR)

( * ) Notice: Subject to any disclaimer, the term of this patent is extended or adjusted under 35 U.S.C. 154(b) by 0 days.

(21) Appl. No.: 18/744,512

(22) Filed: Jun. 14, 2024

(65) Prior Publication Data

US 2025/0017492 A1 Jan. 16, 2025

(30) Foreign Application Priority Data

Jul. 10, 2023 (KR) ........................ 10-2023-0089056

(51) Int. Cl.
*A61B 5/11* (2006.01)
*A61B 5/00* (2006.01)
(Continued)

(52) U.S. Cl.
CPC ............ *A61B 5/112* (2013.01); *A61B 5/0082* (2013.01); *A61B 5/1126* (2013.01); *G01S 7/4802* (2013.01); *G01S 17/88* (2013.01)

(58) Field of Classification Search
CPC ..... A61B 5/112; A61B 5/0082; A61B 5/1126; G01S 7/4802; G01S 17/88
See application file for complete search history.

(56) References Cited

U.S. PATENT DOCUMENTS 10,873,726 B1 * 12/2020 Maldonado .......... H04N 17/004
2019/0117318 A1 * 4/2019 Charron ............... A61B 5/0077
(Continued)

FOREIGN PATENT DOCUMENTS

KR 101895399 B1 9/2018

OTHER PUBLICATIONS

Benedek, C., et al., "Lidar-based Gait Analysis and Activity Recognition in a 4D Surveillance System," IEEE Trans. Circuits and Systems for Video Technology. vol. 28(1), 2016. p. 1-13 (Year: 2016).*

(Continued)

*Primary Examiner* — Sean A Frith
(74) *Attorney, Agent, or Firm* — STIP Law Group, LLC

(57) ABSTRACT

Proposed are a gait measurement system and method using a LiDAR adjacent to a floor. More specifically, the system includes a walking path for a measurement subject to walk, a LiDAR sensor device installed on the floor at a side of the walking path and configured to scan the walking path, and a gait analysis part configured to use a signal detected by the LiDAR sensor device to analyze a gait of the measurement subject walking on the walking path. The method includes collecting scanning data obtained by the LiDAR sensor device scanning the walking path on which the measurement subject is walking, analyzing the scanning data to specify foot positions of the measurement subject, and using the specified foot positions of the measurement subject to analyze at least one selected from a group of step length, the number of steps, and gait speed, from changes in the foot positions.

7 Claims, 6 Drawing Sheets

(51) Int. Cl.
*G01S 7/48* (2006.01)
*G01S 17/88* (2006.01)

(56) References Cited

U.S. PATENT DOCUMENTS

| | | | | |
|---|---|---|---|---|
| 2021/0321971 | A1* | 10/2021 | Junio | A61B 6/0492 |
| 2022/0057519 | A1* | 2/2022 | Goldstein | G01S 17/88 |
| 2022/0331028 | A1* | 10/2022 | Sternitzke | G05D 1/0094 |
| 2023/0241483 | A1* | 8/2023 | Yoo | G01S 17/89<br>434/247 |
| 2024/0108235 | A1* | 4/2024 | Lee | A61B 5/0261 |

OTHER PUBLICATIONS

Nitschke, M., et al., "Change the direction: 3D optimal control simulation by directly tracking marker and ground reaction force data," PeerJ. vol. 11, 2023. p. 1-21 (Year: 2023).*
Chang, M., et al., "The parameters of gait analysis related to ambulatory and balance functions in hemiplegic stroke patients: a gait analysis study," BMC Neurology. vol. 21(38), 2021. p. 1-8 (Year: 2021).*
Yoon, S., et al., "Development and Validation of 2D-LiDAR-Based Gait Analysis Instrument and Algorithm," Sensors. vol. 21, 2021. p. 1-13 (Year: 2021).*

* cited by examiner

GAIT MEASUREMENT SYSTEM AND METHOD USING LIDAR ADJACENT TO FLOOR

CROSS-REFERENCE TO RELATED APPLICATION

The present application claims priority to Korean Patent Application No. 10-2023-0089056, filed Jul. 10, 2023, the entire contents of which is incorporated herein for all purposes by this reference.

BACKGROUND OF THE INVENTION

Field of the Invention

The present disclosure relates to a gait measurement system and method. More particularly, the present disclosure relates to a gait measurement system and method using a LiDAR adjacent to a floor.

Description of the Related Art

The description in this section merely provides background information on one embodiment of the present disclosure and does not constitute the related art.

Gait analysis is intended to identify idiosyncrasies in the way a person walks, and measures several aspects of a gait to provide a comprehensive evaluation. More specifically, gait analysis may include kinematic analysis, dynamic electromyography, and energy expenditure measurement. Gait analysis may be applied to understand the characteristics of posture or movement of people with leg lesions and spinal misalignment, or to help athletes run more efficiently.

Currently, gait analysis in rehabilitation medicine measures and analyzes a gait using expensive load-measuring mattresses or high-speed cameras. However, this type of gait measurement requires various sensors to be attached to a subject's body, is expensive, and requires a long preparation time for measurement. In addition, the gait measurement is performed in a controlled environment of a laboratory, so there is a limitation in analyzing a gait in daily life.

In recent years, modern people have been spending more time sitting, which has led to an increase in scoliosis, pelvic distortion, and flat feet, and these problems affect gait. Especially for children and teenagers, it is important to recognize and correct poor posture early and develop good gait habits.

As such, there is a growing need for gait measurement and analysis, but it is difficult to easily access conventional gait analysis methods due to costs and limitations. Therefore, there is a need to develop technologies that make gait analysis easier and less expensive.

In the meantime, as a related art of the present disclosure, Korean Patent No. 10-1895399 (invention title: GAIT ANALYSIS AND CORRECTION APPARATUS BASE OF INFORMATION AND COMMUNICATIONS TECHNOLOGY, registration date: 30 Aug. 2018) is disclosed.

The above-described background technology is technical information that has been possessed by the present inventor in order to derive the present disclosure or which has been acquired in the process of deriving the present disclosure, and can not necessarily be regarded as well-known technology which has been known to the public prior to the filing of the present disclosure.

SUMMARY OF THE INVENTION

The present disclosure has been made keeping in mind the above problems occurring in the previously proposed methods, and the present disclosure is directed to providing a gait measurement system and method using a LiDAR adjacent to a floor, wherein a LiDAR sensor device is installed on the floor at a side of a walking path, and a signal detected by the LiDAR sensor device is used to analyze a gait of a measurement subject walking on the walking path. Accordingly, by placing the LiDAR sensor device on the floor, gait measurement is performed simply and easily and at low cost without attaching a sensor to the body of the measurement subject, and a gait analysis result is provided to a client terminal and used for understanding gait habits or correcting the gait.

However, the objectives of the present disclosure are not limited thereto, and there may be other objectives. Even if not explicitly mentioned, the objectives or effects that can be understood from the solutions or embodiments are also objectives of the present disclosure.

According to an aspect of the present disclosure, there is provided a gait measurement system using a LiDAR adjacent to a floor, the gait measurement system including:

a walking path for a measurement subject to walk;

a LiDAR sensor device installed on the floor at a side of the walking path and configured to scan the walking path; and a gait analysis part configured to use a signal detected by the LiDAR sensor device to analyze a gait of the measurement subject walking on the walking path.

Preferably, the gait analysis part may be configured to analyze at least one selected from a group of step length, the number of steps, and gait speed.

Preferably, the LiDAR sensor device may be configured to scan the walking path, and a plane at a predetermined height from the floor.

Preferably, a plurality of the LiDAR sensor devices may be installed at intervals of a predetermined distance on the floor at the side of the walking path.

More preferably, the LiDAR sensor devices may be arranged to face each other across the walking path.

Preferably, the gait measurement system may further include a client terminal on which an application program for outputting an analysis result obtained by the gait analysis part is installed.

According to another aspect of the present disclosure, there is provided a gait measurement method using a LiDAR adjacent to a floor to measure a gait of a measurement subject walking on a walking path, the gait measurement method including the steps, each performed by a gait measurement system including the walking path for the measurement subject to walk, a LiDAR sensor device installed on the floor at a side of the walking path and configured to scan the walking path, and a gait analysis part configured to use a signal detected by the LiDAR sensor device to analyze the gait of the measurement subject walking on the walking path, of (1) collecting scanning data obtained by the LiDAR sensor device scanning the walking path on which the measurement subject is walking;

(2) analyzing the scanning data to specify foot positions of the measurement subject; and (3) using the specified foot positions of the measurement subject to analyze at least one selected from a group of step length, the number of steps, and gait speed, from changes in the foot positions.

Preferably, the gait measurement method may further include after the step (3), (4) providing an analysis result obtained in the step (3) to a client terminal on which an application program for outputting the analysis result obtained by the gait analysis part is installed.

According to the gait measurement system and method using a LiDAR adjacent to the floor proposed in the present disclosure, a LiDAR sensor device is installed on the floor at a side of a walking path, and a signal detected by the LiDAR sensor device is used to analyze a gait of a measurement subject walking on the walking path. Accordingly, by placing the LiDAR sensor device on the floor, gait measurement is performed simply and easily and at low cost without attaching a sensor to the body of the measurement subject, and a gait analysis result is provided to a client terminal and used for understanding gait habits or correcting the gait.

Furthermore, various useful advantages and effects of the present disclosure are not limited to the above-described contents, and will be more easily understood in the process of describing specific embodiments of the present disclosure.

BRIEF DESCRIPTION OF THE DRAWINGS

The above and other objectives, features, and other advantages of the present disclosure will be more clearly understood from the following detailed description when taken in conjunction with the accompanying drawings, in which.

DETAILED DESCRIPTION OF THE INVENTION

Figure 1:
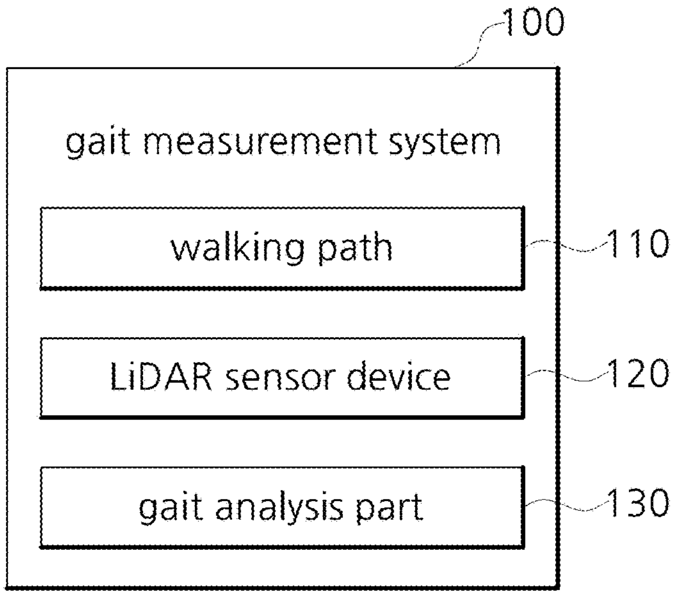
FIG. 1 is a diagram illustrating the configuration of a gait measurement system using a LiDAR adjacent to a floor according to an embodiment of the present disclosure.

Hereinafter, embodiments of the present disclosure will be described in detail with reference to the accompanying drawings such that the present disclosure can be easily embodied by those skilled in the art to which the present disclosure belongs. However, the present disclosure may be embodied in various different forms and should not be limited to the embodiments set forth herein. Further, in order to clearly explain the present disclosure, portions that are not related to the present disclosure are omitted in the drawings, and like reference numerals designate like elements throughout the specification.

Throughout the specification, when a part is referred to as being "connected" to another part, it includes not only being "directly connected", but also being "indirectly connected" by interposing the other part therebetween. In addition, when a part "includes" an element, it is noted that it further includes other elements, but does not exclude other elements, unless specifically stated otherwise, and is not to be understood as precluding the possibility that one or more other features, numbers, steps, operations, elements, parts, or combinations thereof may exist or may be added.

The embodiments described hereinafter are detailed descriptions of the present disclosure to facilitate understanding of the present disclosure and are not intended to limit the scope of the present disclosure. Thus, subject matter having the same scope and performing the same function as that of the present disclosure also falls within the scope of the present disclosure.

In addition, the elements, processes, steps, or methods included in the embodiments of the present disclosure may be shared as long as they do not technically conflict with each other.

In addition, part of the operations or functions described as being performed by a terminal, apparatus, or device in the present disclosure may be performed instead by a server connected to the terminal, apparatus, or device. Similarly, part of the operations or functions described as being performed by the server may be performed by the terminal, apparatus, or device connected to the server.

In particular, the means for executing a system according to each embodiment of the present disclosure may be an application or a web server. Examples of a terminal that is the means for reading a recording medium on which the application or the web server is recorded may include general PCs, such as general desktop and laptop computers, and mobile terminals, such as smartphones and tablet PCs.

Hereinafter, embodiments of the present disclosure will be described in detail with reference to the accompanying drawings.

FIG. 1 is a diagram illustrating the configuration of a gait measurement system 100 using a LiDAR adjacent to a floor according to an embodiment of the present disclosure. As shown in FIG. 1, according to an embodiment of the present disclosure, a gait measurement system 100 using a LiDAR adjacent to a floor includes: a walking path 110 for a measurement subject 10 to walk; a LiDAR sensor device 120 installed on the floor at a side of the walking path 110 and configured to scan the walking path 110; and a gait analysis part 130 configured to use a signal detected by the LiDAR sensor device 120 to analyze a gait of the measurement subject 10 walking on the walking path 110.

Figure 2:
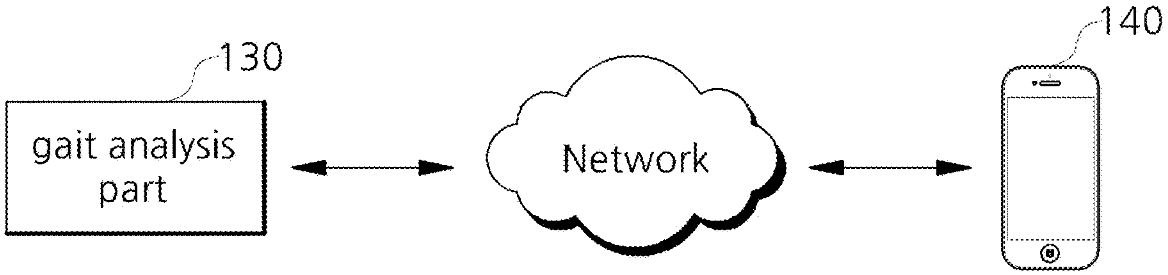
FIG. 2 is a diagram illustrating communication with a client terminal by a gait measurement system using a LiDAR adjacent to a floor according to an embodiment of the present disclosure.

FIG. 2 is a diagram illustrating communication with a client terminal 140 by a gait measurement system 100 using a LiDAR adjacent to a floor according to an embodiment of the present disclosure. As shown in FIG. 2, according to an embodiment of the present disclosure, the gait measurement system 100 using the LiDAR adjacent to the floor may further include the client terminal 140 on which an application program for outputting an analysis result obtained by the gait analysis part 130 is installed.

That is, as shown in FIG. 2, the analysis result obtained by the gait analysis part 130 may be transmitted to the client terminal 140 over a network, and the client terminal 140 may output the analysis result through the application program. Herein, the user of the client terminal 140 may be the measurement subject 10 himself or herself or the measurement subject's 10 guardian, or may be a medical worker or a manager of the gait measurement system 100.

In the meantime, the client terminal 140 may be a portable terminal or a computer. Herein, the portable terminal is a wireless communication device with portability and mobility secured. Examples of the portable terminal may include any types of handheld wireless communication devices, such as personal communication system (PCS), Global System for Mobile communications (GSM), Personal Digital Cellular (PDC), Personal Handy-phone System (PHS), personal digital assistant (PDA), International Mobile Telecommunications (IMT)-2000, code-division multiple access (CDMA)-2000, wideband code-division multiple access (W-CDMA), and wireless broadband Internet (WiBro) terminals. Examples of the computer may include a desktop computer, a notebook computer, and a laptop computer with a web browser.

In addition, the network may be a wired network, such as a local area network (LAN), a wide area network (WAN), or a value-added network (VAN), or any types of wireless networks, such as a mobile radio communication network, a satellite network, Bluetooth, wireless broadband Internet (WiBro), High Speed Downlink Packet Access (HSDPA), long-term evolution (LTE), and 3/4/5/6th-generation mobile telecommunication (3/4/5/6G).

Figure 3:
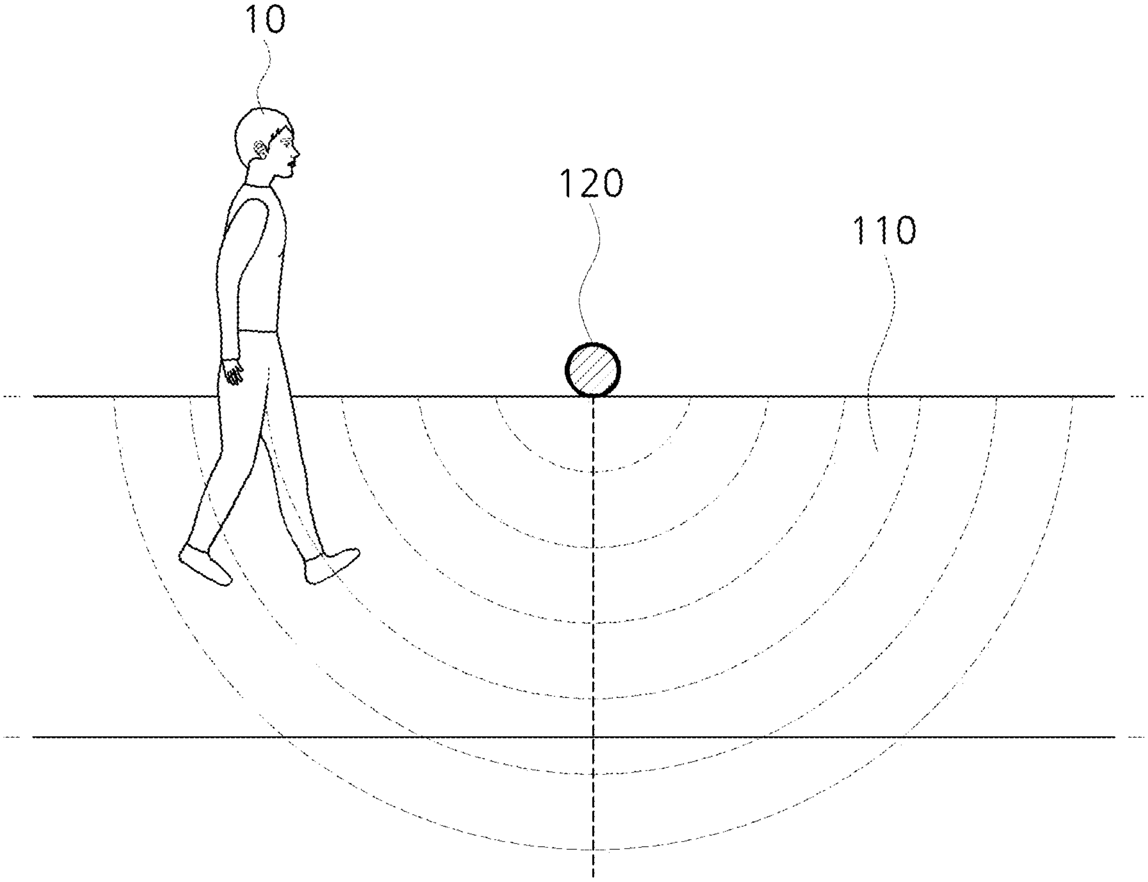
FIG. 3 is a diagram illustrating, as an example, gait measurement through a gait measurement system using a LiDAR adjacent to a floor according to an embodiment of the present disclosure.

FIG. 3 is a diagram illustrating, as an example, gait measurement through a gait measurement system 100 using a LiDAR adjacent to a floor according to an embodiment of the present disclosure. Hereinafter, each element of a gait measurement system 100 using a LiDAR adjacent to a floor according to an embodiment of the present disclosure will be described in detail with reference to FIGS. 1 to 3.

The walking path 110 may be a floor surface for the measurement subject 10 to walk. Herein, the walking path 110 may have a width and length sufficient for the measurement subject 10 to walk comfortably, and may be realized in any place, as it can serve as a walking path 110 even in a narrow space, such as a passage of a building, as long as a walking distance is sufficient.

Depending on an embodiment, an indicative line or an arrow indicating the walking direction or walking course for the measurement subject 10 may be marked on the walking path 110. However, when the walking course is explicitly marked, the measurement subject 10 tries to walk according to the walking course, which may result in an intentional gait rather than a natural gait. Therefore, in order to obtain natural walking data, the walking direction or course may be marked with an arrow or an area in the longitudinal direction of the walking path 110 that is not a straight line and has a width ranging from about 20 to 60 cm, which is human shoulder width.

The LiDAR sensor device 120 may be installed on the floor at a side of the walking path 110 to scan the walking path 110. As shown in FIG. 3, the LiDAR sensor device 120 is installed on the floor at the side of the walking path 110 rather than in the middle of the walking path 110 so that the LiDAR sensor device 120 does not interfere with the gait of the measurement subject 10 and a scanning area covers the entirety of the walking path 110. In addition, the LiDAR sensor device 120 scans the walking path 110, and a plane at a predetermined height above the floor. When the LiDAR sensor device 120 is installed on the floor, the laser scanning height may range from about 3 to 10 cm, more specifically, 5 cm, above the floor. The LiDAR sensor device 120 may generate scanning data by scanning, with lasers, the plane parallel to the floor and at the height of 3 to 10 cm above the floor.

The gait analysis part 130 may use a signal detected by the LiDAR sensor device 120 to analyze the gait of the measurement subject 10 walking on the walking path 110. First, the gait analysis part 130 may receive scanning data generated by the LiDAR sensor device 120 and recognize the positions of the feet of the measurement subject 10 from the scanning data. The gait analysis part 130 may use the recognized positions of the feet to analyze at least one selected from the group of step length, the number of steps, and gait speed. In addition, the positions of the left foot and the right foot and the respective step distances of the left foot and the right foot may be used to analyze left and right gait balance. Depending on an embodiment, the gait analysis part 130 may recognize the angles of the feet of the measurement subject 10 from the scanning data.

Figure 4:
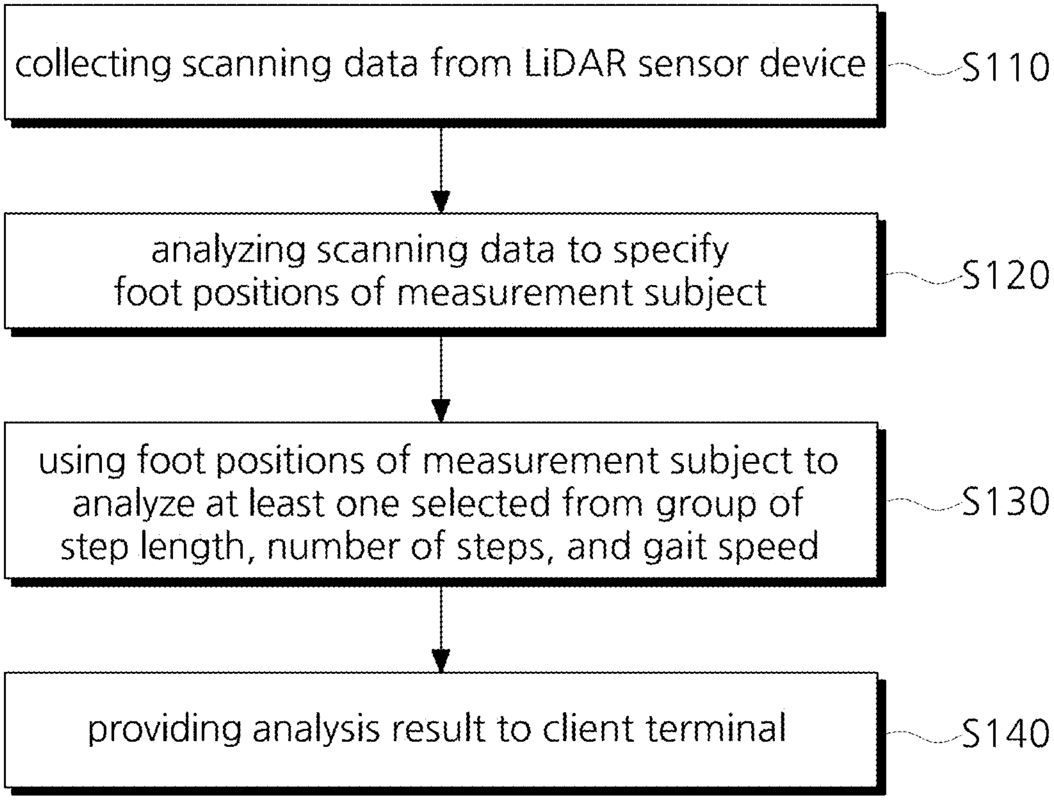
FIG. 4 is a diagram illustrating the flow of a gait measurement method using a LiDAR adjacent to a floor according to an embodiment of the present disclosure.

FIG. 4 is a diagram illustrating the flow of a gait measurement method using a LiDAR adjacent to a floor according to an embodiment of the present disclosure. As shown in FIG. 4, according to an embodiment of the present disclosure, a gait measurement method using a LiDAR adjacent to a floor is a gait measurement method of measuring a gait of a measurement subject 10 walking on a walking path 110. Each step of the gait measurement method is performed in a gait measurement system 100 including: a walking path 110 for a measurement subject 10 to walk; a LiDAR sensor device 120 installed on the floor at a side of the walking path 110 and configured to scan the walking path 110; and a gait analysis part 130 configured to use a signal detected by the LiDAR sensor device 120 to analyze a gait of the measurement subject 10 walking on the walking path 110. The gait measurement method may include: collecting scanning data from the LiDAR sensor device 120 in step S110; analyzing the scanning data to specify foot positions of the measurement subject 10 in step S120; and using the foot positions of the measurement subject 10 to analyze at least one selected from the group of step length, the number of steps, and gait speed in step S130. The gait measurement method may further include providing an analysis result to a client terminal 140 in step S140.

In step S110, the scanning data obtained by the LiDAR sensor device 120 scanning the walking path 110 on which the measurement subject 10 is walking may be collected. That is, in the gait measurement environment as shown in FIG. 3, the scanning data obtained by the LiDAR sensor device 120 when the measurement subject s walking on the walking path 110 may be collected.

In step S120, the scanning data may be analyzed to specify the foot positions of the measurement subject 10. Herein, the positions of the feet of the measurement subject 10 are specified from the scanning data and analyzed in synchronization with the measurement time, and both the positions and angles of the feet may be recognized.

In step S130, the specified foot positions of the measurement subject 10 may be used to analyze at least one selected from the group of the step length, the number of steps, and the gait speed, from changes in the foot positions. In addition, left and right gait balance may be analyzed. In step S130, the step length, the number of steps, the gait speed, and the left and right gait balance may be processed into a form, such as a score or graph, which enables intuitive user understanding.

In step S140, the analysis result obtained in step S130 may be provided to the client terminal 140 on which an application program for outputting the analysis result obtained by the gait analysis part 130 is installed. That is, the gait analysis result, such as the step length, the number of steps, the gait speed, and the left and right gait balance may be provided to the client terminal 140 over the network. The measurement subject 10 himself or herself, a guardian, a medical worker, or a manager may check the gait analysis result through the client terminal 140 and use the gait analysis result for understanding the gait habits or correcting the gait.

Figure 5:
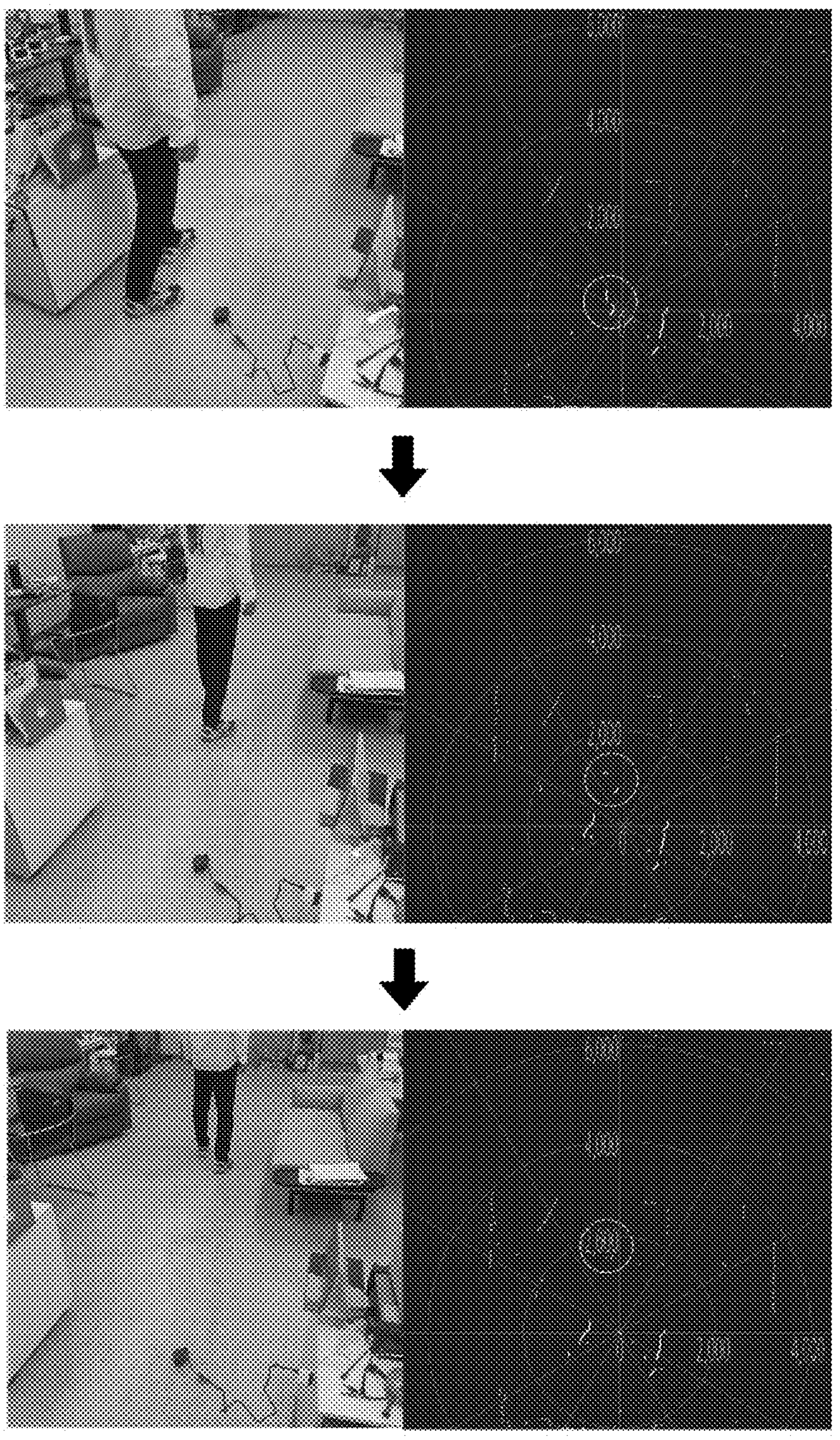
FIG. 5 is a diagram illustrating gait measurement experiment and scanning data from a gait measurement system using a LiDAR adjacent to a floor according to an embodiment of the present disclosure.

FIG. 5 is a diagram illustrating gait measurement experiment and scanning data from a gait measurement system 100 using a LiDAR adjacent to a floor according to an embodiment of the present disclosure. The left of FIG. 5 is photographs of gait measurement, and the right of FIG. 5 is images showing the foot positions of the measurement subject 10 in the scanning data. The gait measurement system 100 using a LiDAR adjacent to a floor according to an embodiment of the present disclosure recognizes the foot positions of the measurement subject 10 accurately even in a narrow space as shown in the left photographs of the gait. As shown in the canning data of the LiDAR sensor device 120 in the right of FIG. 5, the gait analysis part 130 may specify the foot positions (indicated by the yellow dashed circle) of the measurement subject 10, and analyze changes in the foot positions to analyze step length, the number of steps, and gait speed.

Figure 6:
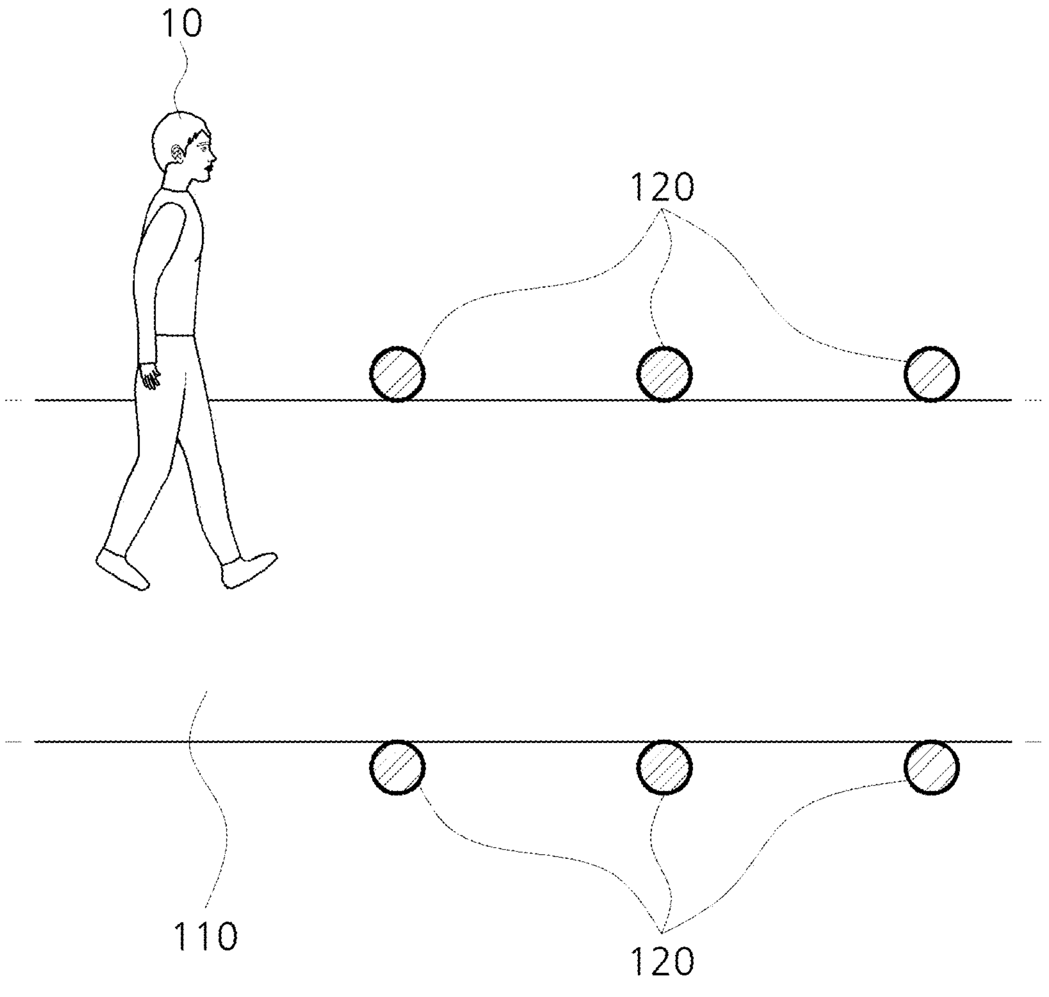
FIG. 6 is a diagram illustrating a plurality of LiDAR sensor devices arranged in a gait measurement system using a LiDAR adjacent to a floor according to an embodiment of the present disclosure.

FIG. 6 is a diagram illustrating a plurality of LiDAR sensor devices 120 arranged in a gait measurement system 100 using a LiDAR adjacent to a floor according to an embodiment of the present disclosure. As shown in FIG. 6, in the gait measurement system 100 using a LiDAR adjacent to a floor according to an embodiment of the present disclosure, the LiDAR sensor devices 120 may be installed at intervals of a predetermined distance on the floor at a side of the walking path 110. According to the characteristics of a LiDAR sensor, the closer a subject is to the sensor, the more accurately the subject is recognized due to higher precision of the sensor in azimuth. Therefore, as shown in FIG. 6, the use of the plurality of LiDAR sensor devices 120 enables the positions of the feet of the measurement subject 10 to be more precisely recognized.

Depending on an embodiment, the LiDAR sensor devices 120 may be arranged to face each other across the walking path 110. By arranging the LiDAR sensors facing to each other, the angles and shapes of the feet of the measurement subject 10 are more accurately recognized, so that additional gait characteristics, such as an out-toed gait, may be analyzed.

Figure 7:
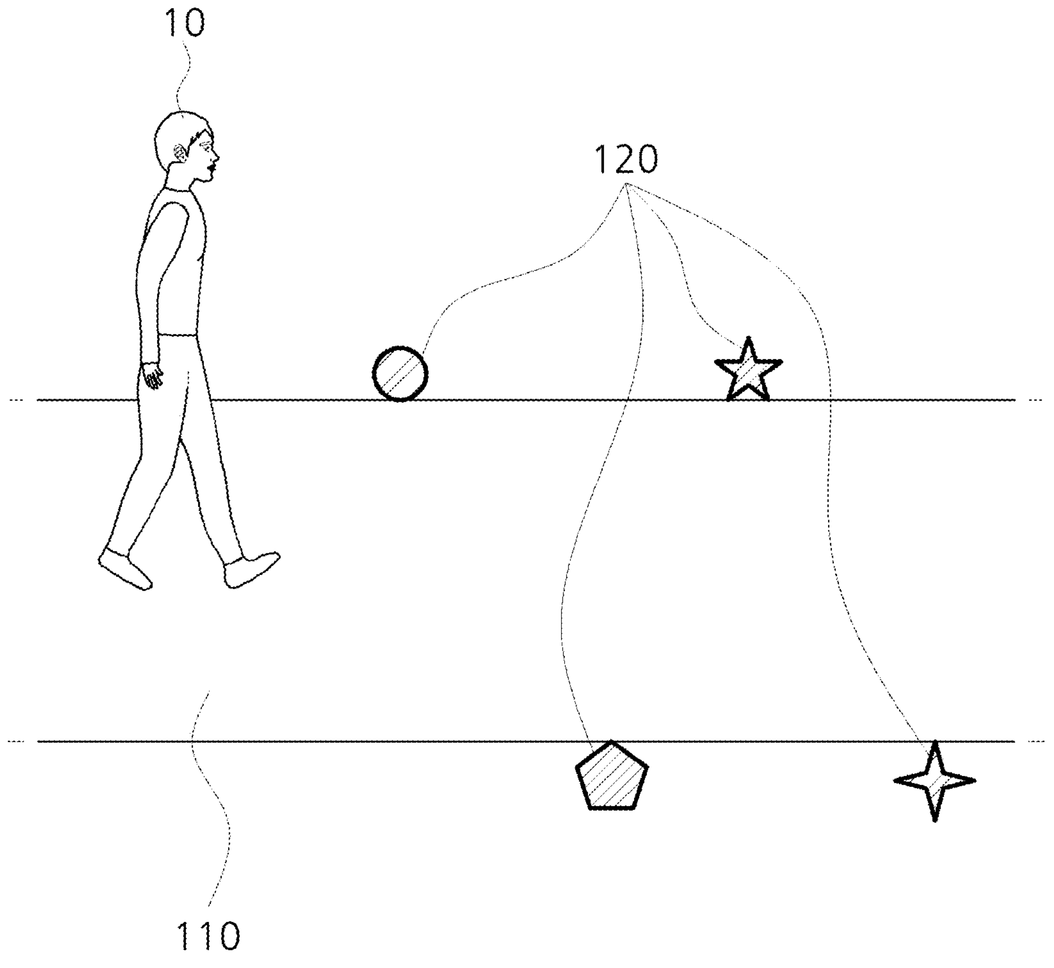
FIG. 7 is a diagram illustrating a plurality of LiDAR sensor devices of different shapes arranged in a gait measurement system using a LiDAR adjacent to a floor according to an embodiment of the present disclosure.

FIG. 7 is a diagram illustrating a plurality of LiDAR sensor devices 120 of different shapes arranged in a gait measurement system 100 using a LiDAR adjacent to a floor according to an embodiment of the present disclosure. As shown in FIG. 7, in the gait measurement system 100 using a LiDAR adjacent to a floor according to an embodiment of the present disclosure, a LiDAR sensor device 120 includes a casing in which a LiDAR sensor is embedded. When there are a plurality of LiDAR sensor devices 120, the casings may have different shapes to enable the LiDAR sensor devices 120 to be specified from scanning data of the different LiDAR sensor devices 120. Therefore, when a plurality of LiDAR sensor devices 120 are used, casings of different shapes may be used as shown in FIG. 7. When a LiDAR sensor device 120 of a circular shape recognizes a star or pentagonal shape, it is easily understood that the recognized object is another LiDAR sensor device 120. In this way, a plurality of LiDAR sensor devices 120 understand each other's locations from their shapes, so that a sensor recognizes the coordinates of the other sensors and the distances to the other sensors and scanning data is accurately mapped. Thus, through accurate mapping of a plurality of pieces of scanning data, the coordinates of the foot positions and the angles and shapes of the feet may be specified with high accuracy.

In the meantime, the gait analysis part 130 may predict a type of a disease from a gait analysis result by using an artificial intelligence model. The artificial intelligence model is trained using step length, the number of steps, gait speed, left and right gait balance, and foot angles as input and types of diseases as output. That is, the step length, the number of steps, the gait speed, the left and right gait balance, and the foot angles that are the gait analysis result of the measurement subject 10 analyzed by the gait analysis part 130 are input to the artificial intelligence model, and a type of a predicted disease, such as musculoskeletal disorders, vestibular disorders, Parkinson's disease, or dementia, may be obtained as output. The output value may be provided to the client terminal 140 of the medical worker to assist in the medical worker's judgment.

Herein, a learning algorithm of the artificial intelligence model may be any one of the following: random forest, convolutional neural network (CNN), a recurrent neural network (RNN), and a transformer. Alternatively, an ensemble algorithm that is a combination of two or more algorithms may be used.

Depending on an embodiment, transfer learning may be used. Transfer learning is the reuse of a pre-trained model for a new problem. Since an already trained model is used, a neural network is deeply trained with relatively little data. In addition, it is also useful because most real problems do not typically have millions of labeled data to train complex models. In the present disclosure, transfer learning may be used to generate, from the artificial intelligence model pre-trained with a large amount of data, group-specific artificial intelligence models for measurement subjects 10 grouped by sex or age, thereby predicting a type of a disease more minutely and accurately.

As described above, according to a gait measurement system 100 and method using a LiDAR adjacent to a floor proposed in the present disclosure, a LiDAR sensor device 120 is installed on the floor at a side of a walking path 110, and a signal detected by the LiDAR sensor device 120 is used to analyze a gait of a measurement subject 10 walking on the walking path 110. Accordingly, by placing the LiDAR sensor device 120 on the floor, gait measurement is performed simply and easily and at low cost without attaching a sensor to the body of the measurement subject 10, and a gait analysis result is provided to a client terminal 140 and used for understanding gait habits or correcting the gait.

In the meantime, the present disclosure may include a computer-readable recording medium including program instructions for performing operations realized by various communication terminals. Examples of the computer-readable recording medium include magnetic recording media such as hard disks, floppy disks and magnetic tapes; optical data storage media such as CD-ROMs or DVD-ROMs; magneto-optical media such as floptical disks; and hardware devices, such as read-only memory (ROM), random-access memory (RAM), and flash memory, which are particularly structured to store and implement the program instructions.

The computer-readable recording medium may include program instructions, data files, data structures, and the like separately or in combinations. Herein, the program instructions being recorded in the computer-readable medium may correspond to program instructions that are specifically designed and configured for the embodiments of the present disclosure, or may correspond to program instructions that are disclosed and available to anyone skilled in the art of computer software. For example, the program commands may include machine language codes, which are created by a compiler, as well as high-level language codes, which may be executed by a computer by using an interpreter.

Although the present disclosure has been described in connection with specific embodiments, some or all of the elements or operations of the embodiments can be realized using a computer system having a general purpose hardware architecture.

The foregoing description of the present disclosure is intended for exemplifications, and it will be understood by those skilled in the art that the present disclosure may be easily modified in other specific forms without changing the technical idea or essential features of the present disclosure. Therefore, it should be understood that the embodiments described above are illustrative in all aspects as and not restrictive. For example, each element described as a single type may be implemented in a dispersed form, and likewise elements described as dispersed may be implemented in a combined form.

The scope of the present disclosure is characterized by the appended claims rather than the detailed description described above, and it should be construed that all alterations or modifications derived from the meaning and scope of the appended claims and the equivalents thereof fall within the scope of the present disclosure.

What is claimed is:

1. A gait measurement system (100) using a LiDAR adjacent to a floor, the gait measurement system comprising:

a walking path (110) for a measurement subject (10) to walk, wherein a walking direction or course is marked by an arrow, or by a non-linear area extending in a longitudinal direction of the walking path (110), the non-linear area having a width ranging from 20 to 60 cm;

a plurality of LiDAR sensor devices (120) installed at intervals of a predetermined distance on the floor adjacent to the walking path (110), each configured to scan the walking path (110), wherein scanning areas of the plurality of LiDAR sensor devices (120) collectively cover the entirety of the walking path (110), wherein each LiDAR sensor device (120) generates respective scanning data by scanning, with lasers, a plane parallel to the floor at a height of 3 cm to 10 cm above the floor, and wherein the plurality includes a first LiDAR sensor device including a first casing having a first casing shape and generating first scanning data and a second LiDAR sensor device including a second casing having a second casing shape different from the first casing shape and generating second scanning data, the second casing shape being recognizable in the first scanning data; and a computing device (130) comprising a processor and a memory storing instructions that, when executed by the processor, cause the computing device (130) to:

identify, in the first scanning data, the second LiDAR sensor device based on the second casing shape;

determine a relative position and a distance between the first and second LiDAR sensor devices based on a position of the identified second LiDAR sensor device in the first scanning data;

map the first and second scanning data based on the determined relative position and distance;

recognize foot positions and toe-out angles (foot angles indicative of an out-toed gait) of the measurement subject (10) from the mapped first and second scanning data; and analyze, based on changes in the foot positions and the toe-out angles, at least one selected from a group consisting of step length, number of steps, gait speed, and left-right gait balance, wherein the left-right gait balance is analyzed based on positions of a left foot and a right foot and respective step distances of the left foot and the right foot.

2. The gait measurement system of claim 1, wherein the instructions further cause the computing device (130) to predict a type of disease by inputting the step length, number of steps, gait speed, left-right gait balance, and the toe-out angles into a trained artificial intelligence model, wherein transfer learning is used to generate, from an artificial intelligence model pre-trained with a large amount of data, group-specific artificial intelligence models for measurement subjects (10) grouped by at least one of sex and age.

3. The gait measurement system of claim 1, wherein the first casing shape and the second casing shape are selected from the group consisting of a circular shape, a star shape, and a pentagonal shape, and are different from each other.

4. The gait measurement system of claim 3, wherein the first LiDAR sensor device and the second LiDAR sensor device are arranged on opposite sides of, and face each other across, the walking path (110).

5. The gait measurement system of claim 1, further comprising a client terminal (140) on which an application program for outputting an analysis result obtained by the computing device (130) is installed, wherein the analysis result is processed into a form of a score or graph for display.

6. A gait measurement method using a plurality of LiDAR sensor devices adjacent to a floor to measure a gait of a measurement subject (10) walking on a walking path (110), the gait measurement method comprising:

collecting first scanning data generated by a first LiDAR sensor device and second scanning data generated by a second LiDAR sensor device, the first and second LiDAR sensor devices being included in a plurality of LiDAR sensor devices (120) installed at intervals of a predetermined distance on the floor adjacent to the walking path (110), wherein a walking direction or course is marked by an arrow, or by a non-linear area extending in a longitudinal direction of the walking path (110), the non-linear area having a width ranging from 20 cm to 60 cm, wherein scanning areas of the plurality of LiDAR sensor devices (120) collectively cover the entirety of the walking path (110), wherein each LiDAR sensor device (120) generates scanning data by scanning, with lasers, a plane parallel to the floor at a height of 3 cm to 10 cm above the floor, wherein the first LiDAR sensor device includes a first casing having a first casing shape, wherein the second LiDAR sensor device includes a second casing having a second casing shape different from the first casing shape, and wherein the second casing shape is recognizable in the first scanning data;

identifying, in the first scanning data, the second LiDAR sensor device based on the second casing shape;

determining a relative position and a distance between the first and second LiDAR sensor devices based on a position of the identified second LiDAR sensor device in the first scanning data;

mapping the first and second scanning data based on the determined relative position and distance;

recognizing foot positions and toe-out angles (foot angles indicative of an out-toed gait) of the measurement subject (10) from the mapped first and second scanning data data; and analyzing, based on changes in the foot positions and the toe-out angles, at least one selected from a group consisting of step length, number of steps, gait speed, and left-right gait balance, wherein the left-right gait balance is analyzed based on positions of a left foot and a right foot and respective step distances of the left foot and the right foot.

7. The gait measurement method of claim 6, further comprising after the analyzing, providing the analysis result to a client terminal (140) on which an application program for outputting the analysis result is installed, wherein the analysis result is processed into a form of a score or graph for display.

* * * * *